US006265160B1

(12) United States Patent
Leonard (10) Patent No.: US 6,265,160 B1
(45) Date of Patent: **\*Jul. 24, 2001**

(54) METHOD OF IDENTIFYING INHIBITORS OF THE JAK-STAT SIGNAL TRANSDUCTION PATHWAY

(75) Inventor: Warren J. Leonard, Bethesda, MD (US)

(73) Assignee: The United States of America as represented by the Department of Health and Human Services, Washington, DC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/003,903

(22) Filed: Jan. 7, 1998

Related U.S. Application Data

(63) Continuation of application No. PCT/US96/11206, filed on Jul. 2, 1996
(60) Provisional application No. 60/000,971, filed on Jul. 7, 1995.

(51) Int. Cl.[7] .................................................... C12Q 1/68
(52) U.S. Cl. ............................ 435/6; 435/7.92; 436/504; 530/350; 530/351; 530/358; 530/395; 530/412
(58) Field of Search ...................... 435/6, 7.92; 436/504; 530/350, 351, 358, 395, 412

(56) References Cited

U.S. PATENT DOCUMENTS

| 5,463,023 | 10/1995 | Schreiber et al. | .................... 530/327 |
|---|---|---|---|
| 5,582,999 | 12/1996 | Schreiber et al. | ..................... 435/7.1 |
| 5,728,536 | 3/1998 | Ihle et al. | ............................ 435/7.21 |
| 5,731,155 | 3/1998 | Schreiber et al. | ..................... 435/7.1 |

FOREIGN PATENT DOCUMENTS

| 9503701 | * | 2/1995 | (WO) . |
|---|---|---|---|
| WO 95/03701 | | 2/1995 | (WO) . |
| WO 95/08001 | | 3/1995 | (WO) . |
| 9511312 | * | 4/1995 | (WO) . |
| WO 95/11312 | | 4/1995 | (WO) . |
| WO 95/28482 | | 10/1995 | (WO) . |
| WO 96/20954 | | 7/1996 | (WO) . |

OTHER PUBLICATIONS

Asao, et al., Interleukin 2 (IL–2)–Induced Tyrosine Phosphorylation of IL–2 Receptor p75; *J. Exp. Med.* 171:637–644 (1990).

Asao, et al., Interleukin 2–induced activation of JAK3: possible involvement in signal transduction for c–myc induction and cell proliferation, *FEBS Letters* 351:201–206 (1994).

Beadling, et al., Activation of JAK kinases and STAT proteins by interleukin–2 and interferon α, but not the T cell antigen receptor, in human T lymphocytes, *The EMBO Journal* 13(23):5605–5615 (1994).

Burns, et al., Interleukin–2–induced Tyrosine Phosphorylation of $p52^{shc}$ in T Lymphocytes, *J. Bio. Chem.* 268(24):17659–17661 (1993).

Harrison, et al., Activation of a *Drosophila janus* kinase (JAK) causes *Hematopoietic neoplasia* and developmental defects, *The EMBO Journal* 14(12):2857–2865 (1995).

Hollsberg, et al., Characterization of HTLV–1 in vivo infected T cell clones: IL–2–Independant Growth of Nontransformed T Cells, *J. Immunol.* 148:3256–3253 (1992).

Izquierdo, et al., The regulation and function of $p21^{ras}$ during T–cell activation and growth, *Immunol. Today* 16(3):159–164 (1995).

Johnston, et al., Phosphorylation and activation of the Jak–3 Janus kinases In response to Interleukin–2, *Nature* 370:151–153 (1991).

Kawamura, et al., Molecular cloning of L–JAK, a Janus famile protein–tyrosine kinase expressed in natural killer cells and activated leukocytes, *Proc. Natl. Acad. Sci. USA* 91:6374–6378 (1994).

Koon, et al., Characterization and Expression of Human JAK3 Splice Variants, *Molecular Oncology–III Abstract* 294a:1161.

Lin, et al., The Role of Shared Receptor Motifs and common Stat Proteins in the Generation of cytokine Pleiotropy and Redundancy by IL–2, IL–4, IL–7, IL–13, and IL–15, *Immunity* 2:331–339 (1995).

Maeda, et al., Evidence for the Interleukin–2 Dependant Expansion of Leukemic Cells in Adult T Cell Leukemia, *Blood* 70(5):1407–1411 (1987).

Mills, et al., Interleukin 2–induced Tyrosine Phosphorylation, *J. Biol. Chem.* 265(6):3561–3567 (1990).

Miyazaki, et al., Functional Activation of Jak1 and Jak3 by Selective Association with IL–2 Receptor Subunits, *Science* 266:1045–1047 (1994).

Nakamura, et al., Heterodimerization of the IL–2 receptor β and γ–chain cytoplasmic domains is required for signalling, *Nature* 369:330–333 (1994).

(List continued on next page.)

*Primary Examiner*—Robert D. Budens
(74) *Attorney, Agent, or Firm*—Knobbe, Martens, Olson & Bear, LLP (57) ABSTRACT

Agents which inhibit the Jak-Stat signal transduction pathway are identified in order to identify candidate drugs for treatment of proliferative disorders. Identification methods are alternatively based on inhibiting the interaction of: (1) the activated Stat3 and Stat5 transcription factors with an electrophoretic mobility shift assay probe, or (2) the Stat3 or Stat5 proteins with the IL-2Rβ chain of the IL-2 receptor.

20 Claims, 3 Drawing Sheets

OTHER PUBLICATIONS

Nelson, et al., Cytoplasmic domains of the interleukin–2 receptor β and γ chains mediated the signal for T–cell proliferation, *Nature* 369:333–336 (1994).

Otani, et al., Interleukin (IL)–2 and IL–3 induce distinct but overlapping responses in murine IL–3–dependent 32D cells transduced with human IL–2 receptor β chain: Involvement of tyrosine kinase(s) other than p56$^{lck}$, *Proc. Natl. Acad. Sci. USA* 89:2789–2793 (1992).

Rane, et al., JAK3: A novel JAK kinase associated with terminal differentiation of hematopoietic cells, *Oncogene* 9:2415–2423 (1994).

Ravichandran et al., The Adapter Protein Shc Interacts with the Interleukin–2 (IL–2) Receptor upon Il–2 Stimulation, *J. Biol. Chem.* 269(3):1599–1602 (1994).

Rohwer, et al., Characterization of an IL–2 dependent human T cell leukemia virus type 1 (HTLV–I) infected cell line: a system for studying HTLV–I mediated transformation, *Intl. J. Oncology* 5:1163–1169 (1994).

Russell, et al., Interaction of IL–2Rβ and γ$_c$ Chains with Jak1 and Jak3: Implications for XSCID and XCID, *Science* 266:1042–1045 (1994).

Safford, et al., JAK3, A member of the JAK family of nonreceptor tyrosine kinases, is expressed in the stem/progenitor cell fraction of human bone marrow, *Hematopoietic Cell Proliferation and Differentiation–II* Abstract 122a:475.

Taniguchi, T., Cytokine Signaling Through Nonreceptor Protein Tyrosine Kinases, *Science* 268:251–255 (1995).

Takahashi, et al.,Molecular cloning of rat JAK3, a novel member of the JAK family of protein tyrosine kinases, *FEBS Letters* 342–124–128 (1994).

Tsudo, et al., Characterization of the interleukin 2 receptor β chain using three distinct monoclonal antibodies, *Proc. Natl. Acad. Sci. USA* 86:1982–1986 (1989).

Whitthun, et al., Involvement of the Jak–3 Janus kinases In signalling by interleukins 2 and 4 In lymphoid and myefold cells, *Nature* 370:153–157 (1994).

Yssel, et al., Human T Cell Leukemia/Lymphoma Virus Type I Infection of a CD4 Proliferative/Cytotoxic T Cell Clone Progresses in at Least Two Distinct Phases Based on Changes in Function and Phenotype of the Infected Cells, *J. Immunol.* 142(7):2279–2289 (1989).

Zeng, et al., JAK3 Janus kinase is involved in interleukin 7 signal pathway, *FEBS Letters* 353:289–293 (1994).

* cited by examiner

SEQUENCE LISTING

<160> NUMBER OF SEQ ID NOS: 13

<210> SEQ ID NO 1
<211> LENGTH: 26
<212> TYPE: DNA
<213> ORGANISM: Artificial Sequence
<220> FEATURE:
<223> OTHER INFORMATION: Oligonucleotide

<400> SEQUENCE: 1
agcttgtatt tcccagaaaa gggatc                                    26

<210> SEQ ID NO 2
<211> LENGTH: 21
<212> TYPE: DNA
<213> ORGANISM: Artificial Sequence
<220> FEATURE:
<223> OTHER INFORMATION: Oligonucleotide

<400> SEQUENCE: 2
catttccatg aattcggatc c                                         21

<210> SEQ ID NO 3
<211> LENGTH: 16
<212> TYPE: PRT
<213> ORGANISM: Artificial Sequence
<220> FEATURE:
<223> OTHER INFORMATION: Peptide

<400> SEQUENCE: 3

Cys Gln Glu Leu Gln Lys Lys Ala Glu His Gln Val Gly Glu Asp Gly
 1               5                  10                  15

<210> SEQ ID NO 4
<211> LENGTH: 58
<212> TYPE: DNA
<213> ORGANISM: Artificial Sequence
<220> FEATURE:
<223> OTHER INFORMATION: Oligonucleotide

<400> SEQUENCE: 4
gatcgaattc atggaaatgg atcgaattca tggaaatgga tcgaattcat ggaaatgc   58

<210> SEQ ID NO 5
<211> LENGTH: 62
<212> TYPE: DNA
<213> ORGANISM: Artificial Sequence
<220> FEATURE:
<223> OTHER INFORMATION: Oligonucleotide

<400> SEQUENCE: 5

```
gatcgtattt cccagaaaag gatcgtattt cccagaaaag gatcgtattt cccagaaaat    60
gc                                                                  62
```

<210> SEQ ID NO 6
<211> LENGTH: 27
<212> TYPE: DNA
<213> ORGANISM: Artificial Sequence
<220> FEATURE:
<223> OTHER INFORMATION: Oligonucleotide

<400> SEQUENCE: 6

```
accaaccagg gtttcttctt cttccac                                       27
```

<210> SEQ ID NO 7
<211> LENGTH: 58
<212> TYPE: DNA
<213> ORGANISM: Artificial Sequence
<220> FEATURE:
<223> OTHER INFORMATION: Oligonucleotide

<400> SEQUENCE: 7

```
atagaggcct gccaggtgtt ctttactttc gaccccttct cagaggaaga ccctgatg    58
```

<210> SEQ ID NO 8
<211> LENGTH: 33
<212> TYPE: DNA
<213> ORGANISM: Artificial Sequence
<220> FEATURE:
<223> OTHER INFORMATION: Oligonucleotide

<400> SEQUENCE: 8

```
gaggacgacg ccttctgcac cttcccctcc agg                                33
```

<210> SEQ ID NO 9
<211> LENGTH: 27
<212> TYPE: DNA
<213> ORGANISM: Artificial Sequence
<220> FEATURE:
<223> OTHER INFORMATION: Oligonucleotide

<400> SEQUENCE: 9

```
aacactgatg ccttcttgtc cctccaa                                       27
```

<210> SEQ ID NO 10
<211> LENGTH: 12
<212> TYPE: PRT
<213> ORGANISM: Artificial Sequence
<220> FEATURE:
<223> OTHER INFORMATION: Peptide

<400> SEQUENCE: 10

```
Glu Asp Asp Ala Tyr Cys Thr Phe Pro Ser Arg Asp
 1               5                  10
```

<210> SEQ ID NO 11
<211> LENGTH: 12
<212> TYPE: PRT
<213> ORGANISM: Artificial Sequence
<220> FEATURE:
<223> OTHER INFORMATION: Peptide

<400> SEQUENCE: 11

```
Asn Thr Asp Ala Tyr Leu Ser Leu Gln Glu Leu Gln
 1               5                  10
```

```
-continued

<210> SEQ ID NO 12
<211> LENGTH: 12
<212> TYPE: PRT
<213> ORGANISM: Artificial Sequence
<220> FEATURE:
<223> OTHER INFORMATION: Peptide
<220> FEATURE:
<221> NAME/KEY: MOD_RES
<222> LOCATION: (5)...(5)
<223> OTHER INFORMATION: Xaa=Phosphotyrosine

<400> SEQUENCE: 12

Thr Asn Gln Gly Xaa Phe Phe Phe His Leu Pro Asp
 1               5                  10

<210> SEQ ID NO 13
<211> LENGTH: 12
<212> TYPE: PRT
<213> ORGANISM: Artificial Sequence
<220> FEATURE:
<223> OTHER INFORMATION: Peptide
<220> FEATURE:
<221> NAME/KEY: MOD_RES
<222> LOCATION: (5)...(5)
<223> OTHER INFORMATION: Xaa=Phosphotyrosine

<400> SEQUENCE: 13

Gln Glu Glu Ala Xaa Val Thr Met Ser Ser Phe Tyr
 1               5                  10
```

METHOD OF IDENTIFYING INHIBITORS OF THE JAK-STAT SIGNAL TRANSDUCTION PATHWAY

RELATED APPLICATIONS

This application is a continuation of prior International Application No. PCT/US96/11206 filed Jul. 2, 1996, which claims priority under 35 U.S.C. §119(e) of Provisional Application No. 60/000,971 filed Jul. 7, 1995.

FIELD OF THE INVENTION

The present invention relates generally to the field of transmembrane signal transduction. More specifically, the invention relates to the biochemical activation of IL-2 inducible transcription factors.

BACKGROUND OF THE INVENTION

The interaction of interleukin-2 (IL-2) with its receptor regulates the magnitude and duration of the T cell response to antigen. IL-2 signalling requires dimerization of the cytoplasmic domains of the β chain (IL-2Rβ) and γ chain (IL-2Rγ) of the IL-2 receptor. IL-2Rγ is referred to as the common cytokine receptor γ chain ($\gamma_c$), because it is a component of the receptors for IL-2, IL4, IL-7, IL-9 and IL-15. Like other members of the cytokine receptor superfamily, neither the IL-2Rβ nor the $\gamma_C$ chain has intrinsic catalytic activity. The IL-2Rβ chain is shared by the receptors for IL-2 and IL-15 (Giri et al., *EMBO J.* 13:2822 (1994)). IL-2 rapidly activates Stat5 in resting peripheral blood lymphocytes (PBL) and activates both Stat5 and Stat3 in PBL that have been protreated with phytohemagglutinin (PHA).

Tyrosine phosphorylation of cellular proteins, including IL-2Rβ (Asao at al., *J Exp. Med.* 171:637 (1990); Mills et al., *J. Biol Chem.* 265:3561 (1990)), is one of the earliest events which follows IL-2 stimulation of responsive target cells. Those having ordinary skill in the art will appreciate that tyrosine phosphorylation can create docking sites for downstream signalling molecules having SH2 domains Signaling molecules in this category include, for example, Shc, Src, Grb2, PI 3-kinase, GAP, PTP-1D, and PLC-γ in the case of the epidermal growth factor receptor, and Zap70 and Syk tyrosine kinases in the case of the T-cell and B-cell antigen receptors.

In contrast to some other signalling systems, phosphotyrosine docking sites have not been shown to be essential for IL-2 induced cellular proliferation. IL-2 signalling requires the heterodimerization of the IL-2β and $\gamma_c$ chain cytoplasmic domains (Nakamura et al., *Nature* 369:330 (1994); Nelson et al., *Nature* 369:333 (1994)). This heterodimerization promotes the interaction of receptor-associated molecules and activates signalling pathways.

SUMMARY OF THE INVENTION

Agents which inhibit the Jak-Stat signal transduction pathway are identified in order to identify candidate drugs for treatment of proliferative disorders. Identification methods are alternatively based on inhibiting the interaction of: (1) the activated Stat3 and Stat5 transcription factors with an electrophoretic mobility shift assay probe, or (2) the Stat3 or Stat5 proteins with the IL-2Rβ chain of the IL-2 receptor.

DETAILED DESCRIPTION OF THE INVENTION

We have discovered that the Jak-Stat biochemical signalling pathway is constitutively activated in HTLV-I infected cells that have progressed to a state of IL-2 independence. We have further discovered that certain tyrosine residues in the cytoplasmic domain of the IL-2Rβ protein are essential for activation of the Stat proteins. Herein we disclose a method of drug discovery useful for identifying compounds that inhibit the Jak-Stat pathway. Drugs identified by this method are candidates for the treatment of proliferative disorders dependent on the Jak-Stat pathway, including those caused by HTLV-I and other retroviral infections.

HTLV-I is a retrovirus that can immortalize and transform human $CD4^+$ T cells. After infection of T cells by HTLV-I, there is an initial phase of IL-2-dependent cell growth, followed by an IL-2-independent phase. This phenomenon has been addressed by Maeda et al. in Blood 70:1407 (1987); Yssie et al., in *J. Immunol.* 142:2279 (1989); Hollsberg et al., in *J. Immunol* 148:3256 (1992) and Rohwer et al., in *Int. J. Oncol* 5:1163 (1994).

To investigate the potential role of the Jak-Stat pathway in HTLV-I-mediated T cell growth, we examined HTLV-I-transformed T cell lines for the presence of nuclear complexes capable of binding to the γ interferon activated sequence (GAS) motif from the FcγRI promoter. This probe was selected because the GAS motif has been shown to bind IL-2-induced complexes in normal PHA-activated PBL (Lin et al. *Immunity* 2:331 (1995)).

Example 1 describes the methods used to demonstrate that the Stat3 and Stat5 transcription factors were constitutively active in HTLV-I transformed T cells.

EXAMPLE 1

Constitutive but Inducible Stat3 and Stat5 Activation in HTLV-I-transformed T Cell Lines Peripheral blood lymphocytes (PBL) that had been obtained from normal donors and then preactivated by treatment with PHA, HTLV-I-transformed MT-2 and HUT-102B2 cells were maintained either as unstimulated controls or stimulated with 2 nM IL-2 for 0, 15 or 30 minutes. Nuclear extracts were prepared from the cells and electrophoretic mobility-shift assays (EMSAs) performed according to the method described by Lin et al. in *Immunity* 2:331 (1995). The FcγRI promoter probe employed in the EMSA procedure had the sequence, 5'-AGCTTGTATTTCCCAGAAAAGGGATC-3' (SEQ ID NO:1), in which the GAS motif is underlined for clarity. PHA-treated PBL were prepared by isolating PBL using Lymphocyte Separation Medium (Organon Teknika, Durham, N.C.), culturing for 72 hours in RPMI 1640 medium containing 10% fetal bovine serum (FBS) and PHA (1 μg/ml, Boehringer Mannheim), and then incubating overnight in RPMI 1640 containing 10% FBS. Cells were washed and resuspended in fresh medium and stimulated with 0 or 2 nM IL-2. MT-2 cells were grown in RPMI 1640 containing 10% FBS, washed, cultured for 4 hours in RPMI 1640 containing 1% FBS, and then resuspended in RPMI 1640 containing 10% FBS for 1 hour before stimulation with 0 or 2 nM IL-2. HUT102B2 cells were treated similarly.

Results of the EMSA procedure indicated a significant difference between the activated transcription factors present in cells that were or were not transformed by HTLV-I. Probe-binding factors were undetectable in nuclear extracts prepared from PHA-treated PBL in the absence of IL-2 stimulation. However, extracts of PHA-treated PBL that had been stimulated with IL-2 for 15 or 30 minutes produced a doublet band on the EMSA autoradiograph. Thus, IL-2 stimulation of PHA-treated PBL induced one or more nuclear factors that bound the gel shift probe. The magnitude of this induction was most dramatic because the binding activity was undetectable in unstimulated cells, but strongly detectable in IL-2 induced cells. In contrast, extracts from unstimulated MT-2 cells contained substantial probe-binding activity that produced a band which comigrated with the slower migrating band observed when extracts from IL-2 induced, PHA-treated PBL were used in the EMSA. The intensities of this band and the faster migrating band of the doublet were increased by IL-2 stimulation relative to that observed when unstimulated MT-2 cells were used to prepare the extracts. Results obtained using extracts from unstimulated and IL-2 stimulated HUT-102B2 cells were substantially identical to those obtained with MT-2 cells.

Thus, in contrast to PHA-treated PBL, in which complexes were seen only after stimulation of cells with IL-2, constitutive complexes were detected in two T cell lines, MT-2 and HUT-102B2 that were transformed with HTLV-I. The fact that IL-2 increased the DNA binding activity in these cells indicated that they retained the ability to transduce IL-2 signals. Notably, these HTLV-I-transformed T cell lines neither produced IL-2 nor required IL-2 for survival. Similar constitutive nuclear complexes were neither observed in T cell lines not transformed by HTLV-I, such as Jurkat and HUT-78 T cells, nor in the absence of IL-2 stimulation in IL-2-dependent CTLL-2 and Kit-225 T cell lines. Of the two complexes detected in PHA-treated PBL that had been stimulated with IL-2, cells transformed with HTLV-I contained more of the slower migrating complex.

Cross-linking of DNA-protein complexes mediated by ultraviolet (UV) irradiation indicated that the same adducts were present in both cell types. Briefly, 30–40 μg of nuclear extracts were preincubated with 4 μg of poly dI:dC in binding buffer prior to addition of 300,000 to 400,000 cpm (1 ng) of probe. To prepare this probe, the bottom strand of the IL-2Rβ oligonucleotide, 5'-CATTTCCATGAATTCGGATCC-3' (SEQ ID NO:2) was labeled by specific priming in the presence of bromodeoxyuridine and [$^{32}$P]dATP. Samples of the extract and probe mixture were irradiated for 30 minutes at 70 watts in a Hoefer UV cross-linker and then resolved on 7.5% SDS gels. For cold competition, the unlabeled oligonucleotide was preincubated for 20 minutes with nuclear extracts prior to addition of probe. Autoradiographic results indicated identical banding patterns when nuclear extracts from either PHA-treated PBL or MT-2 cells were used. This confirmed that the HTLV-I transformed T cell lines constitutively expressed the same probe-binding factor that was strongly induced by IL-2 stimulation of PHA-treated PBL.

As illustrated in the following Example, the tyrosine phosphorylation status of the Stat3 and Stat5 transcription factors was found to differ between PHA-treated PBL and MT-2 cells.

Example 2 describes the methods used to demonstrate high background levels of tyrosine phosphorylation in HTLV-I transformed cells.

EXAMPLE 2

Inducible and Constitutive Tyrosine Phosphorylation of Stat3 and Stat5

Samples of PHA-treated PBL and MT-2 cells (15×10$^6$ to 10×10$^6$) were left as untreated controls or stimulated with 2 nM IL-2 for 10 minutes at 37° C., washed twice with phosphate-buffered saline (PBS), and lysed in 10 mM tris (pH 7.5) containing 2 mM EDTA, 0.15 M NaCl, 0.875% Brij 96, 0.125% Nonidet P40, 0.4 mM sodium vanadate, 1 mM 4-(2-aminoethyl)-benzenesulfonyl fluoride hydrochlorine (ICN), 2.5 mM leupeptin, and 2.5 mM aprotinin. Immunoprecipitations were performed using anti-Stat3 antiserum (Santa Cruz Biotechnology) or R1146 anti-Stat5 antiserum. The R1146 anti-human Stat5 antiserum was produced by immunizing rabbits with a peptide that corresponded to amino acids 66–80 of human Stat5 synthesized on an Applied Biosystems 431A peptide synthesizer using a MAP 8 branched resin (Applied Biosystems). The oligopeptide used in this procedure had the amino acid sequence, CQELQKKAEHQVGEDG (SEQ ID NO:3). Immunoprecipitates were separated by SDS-PAGE (8% gel), transferred to immobilon P membranes (Millipore, Bedford, Mass.), immunoblotted with antibody to phosphotyrosine 4G10 (UBI, Lake Placid, N.Y.), and developed with enhanced chemiluminescence (ECL, Amersham).

Results indicated that both Stat3 and Stat5 were tyrosine phosphorylated in response to IL-2 stimulation of PHA-treated PBL. These same Stat proteins were constitutively tyrosine phosphorylated in MT-2 cells, and their phosphorylation was increased in cells treated with IL-2. These results demonstrated that the Stat3 and Stat5 transcription factors exhibited high background levels of tyrosine phosphorylation in unstimulated cells that were transformed by HTLV-I. This phenomenon clearly distinguished HTLV-I transformed T cells from their non-transformed counterparts.

To confirm the presence of Stat3 and Stat5 in the nuclear complexes formed from MT-2 cells, we purified complexes that bound to a multimerized GAS probe. Proteins in the complex were separated by SDS-polyacrylamide gel electrophoresis (PAGE) and detected by protein immunoblotting with antisera to Stat3 and Stat5.

Example 3 describes the methods used to demonstrate that Stat3 and Stat5 proteins complexed with the GAS motif probe.

EXAMPLE 3

Affinity Purification of DNA Binding Proteins and Immunoblotting

Nuclear extracts were incubated on ice for 15 minutes in a final volume of 200 μl binding buffer (12 mM HEPES [pH 7.9], 20 mM KCl, 0.5 mM EDTA, 0.5 mM DTT, 1 mM AEBSF, 10% glycerol) containing 4–16 μg of poly dI:dC (Boehringer-Mannheim). Then 40–160 ng biotinylated double-stranded oligonucleotides containing the GAS motifs from IL-2Rβ (5'-biotin-GATCGAATTCATGGAAATGGATCGAATTCATGGA AATGGATCGAATTCATGGAAATGA-3' (SEQ ID NO:4)) or FcγRI (5'-biotin-GATCGTATTTCCCAGAAAAGGATCGTATTTCCC AGAAAAGGATCGTATTTCCCAGAAAATGC-3(SEQ ID NO:5))gene (Midland Reagent Company) was added and the incubation continued for 15 minutes at room temperature. The reaction was added to streptavidin coated magnetic beads (Promega) that had been washed three times in washing buffer (12 mM HEPES [pH 7.9], 100 mM KCl, mM EDTA, DTT, 12% glycerol, 1 mM AEBSF, 0.05% NP40, 100 mg/ml bovine serum albumin) and incubated for 30 minutes on ice. The beads were then washed three times with washing buffer containing 33 μg/ml poly dI:dC. The bound proteins eluted with Laemmli sample buffer, separated on 8% SDS-PAGE (Novex), blotted to Immobilon-P membranes, and Western analyses performed using either 4G10, anti-Stat3 or anti-Stat5 monoclonal antibodies (mAbs), and developed using enhanced chemiluminescence (Amersham).

Results of the affinity purification and immunoblotting procedure confirmed that Stat3 and Stat5 bound the polynucleotide containing the GAS motif in both PHA-treated and IL-2 stimulated PBL and in MT-2 cells. More specifically, autoradiographic results indicated that anti-Stat3 antiserum identified doublet protein bands having molecular weights slightly less than 98 kDa, but greater than 64 kDa, in lanes corresponding to both affinity purified products from both PHA-treated and IL-2 stimulated PBL and MT-2 cells. Similarly, the anti-Stat5 antiserum identified single bands for both samples of affinity purified products. Thus, the DNA-protein complexes that were constitutive in HTLV-I transformed T cells contained the Stat3 and Stat5 transcription factors. These same complexes were formed in PHA-treated PBL upon stimulation with IL-2.

Since HTLV-I does not encode any proteins with intrinsic tyrosine kinase domains, we postulated that cellular tyrosine kinases mediated the activation of Stat3 and Stat5 in MT-2 cells. Because Jak1 and Jak3 are known to be activated in cells treated with IL-2, we investigated the tyrosine phosphorylation status of these kinases in MT-2 cells. As disclosed in the following Example, we discovered that Jak1 and Jak3 were not tyrosine phosphorylated in PHA-treated PBL or in natural killer (NK)-like YT cells in the absence of IL-2, but were constitutively phosphorylated in MT-2 cells. This led to the conclusion that Jak1 and Jak3 mediated constitutive Stat activation in HTLV-I transformed cells, as represented by the MT-2 cell line.

Example 4 describes the methods used to demonstrate that the Jak1 and Jak3 proteins exhibited constitutive levels of tyrosine phosphorylation in MT-2 cells. Significantly, the level of tyrosine phosphorylation of the Jak1 and Jak3 proteins was further increased by IL-2 stimulation.

EXAMPLE 4

Constitutive but Inducible Jak3 Tyrosine Phosphorylation in an HTLV-I-Transformed T Cell Line YT cells or MT-2 cells were left as untreated controls or stimulated with 2 nM IL-2 for 10 minutes. Proteins from cell lysates were immunoprecipitated with antiserum to Jak1 (UBI), electrophoresed and blotted with 4G10 anti-phosphotyrosine antibody according to standard procedures.

Results indicated that Jak1 tyrosine phosphorylation was induced from low background levels to higher levels in both cell lines.

In a parallel procedure, PHA-treated PBL, YT cells and MT-2 cells were left as untreated controls or stimulated with 2 nM IL-2 for 10 minutes. Proteins from cell lysates were immunoprecipitated with antiserum to Jak3 (Kawamura et al., Proc. Natl Acad. Sci U.S.A. 91:6374 (1994)). electrophoresed and blotted with the 4G10 anti-phosphotyrosine antibody.

Results indicated a clear difference between the HTLV-I transformed MT-2 cell line, and the other cells used in the procedure. More specifically, a strong Jak3 signal was observed as a single band between the 97 kDa and 200 kDa markers on the immunoblot following IL-2 induction of either PHA-treated PBL or YT cells, but not in lysates of PHA-treated PBL or YT cells in the absence of IL-2 stimulation. Conversely, a strong constitutive signal representing tyrosine phosphorylated Jak3 was detected in lysates of untreated control MT-2 cells. Interestingly, the intensity of the tyrosine phosphorylated Jak3 band increased in the lanes representing IL-2 induced MT-2 cell lysates. These results indicated that Jak3 was constitutively activated in HTLV-I transformed MT-2 cells. However, the level of tyrosine phosphorylated Jak3 could be increased somewhat in these cells following IL-2 induction.

Because the association of Jak3 with $\gamma_c$, in YT cells (Russell et al., Science 266:1042 (1994)) and PHA-treated PBL is only very weakly detected before stimulation with IL-2 and is potently increased after IL-2 stimulation, we investigated whether Jak3 and $\gamma_c$ were constitutively associated in MT-2 cells.

Example 5 describes the methods used to demonstrate constitutive assembly of IL-2 receptor complexes in HTLV-I transformed cells.

EXAMPLE 5

Constitutive Association of Jak3 and IL-2 Receptor Subunits in HTLV-I-Transformed Cells Samples of YT and MT-2 cells were either left as untreated controls or stimulated with 2 nM IL-2 for 10 minutes. Proteins from cell lysates were immunoprecipitated with mAb 3B5 to $\gamma_c$ (Russell at al., Science 266:1042 (1994)) or mAb Mikβ1 to IL-2Rβ (Tsudo at al., Proc. Natl. Acad. Sci. U.S.A. 86:1982 (1989)), blotted with antiserum to Jak3, and detected by ECL according to standard procedures.

Results of this procedure indicated that Jak3 and $\gamma_c$ were constitutively associated in control MT-2 cells, but not in control YT cells. More specifically, autoradiography revealed a protein band between the 97 kDa and 200 kDa markers, representing Jak3, in immunoprecipitates from IL-2 stimulated MT-2 and YT cells. However, while lanes corresponding to immunoprecipitates from unstimulated YT cells lacked a Jak3 band, those representing unstimulated MT-2 cells had a clearly evident Jak3 band. The intensity of the Jak3 bands on the autoradiograph were substantially similar in lanes representing immunoprecipitates from MT-2 cells that were or were not stimulated by IL-2. Identical results were obtained when anti-$\gamma_c$ or anti-IL-2Rβ antibodies were used to perform the immunoprecipitation step. Indeed, both $\gamma_c$ and Jak3 were constitutively coprecipitated with IL-2Rβ in MT-2 cells. $\gamma_c$ and Jak3 ordinarily interact with IL-2Rβ only in cells stimulated with IL-2.

Thus, a mAb to $\gamma_c$ coprecipitated Jak3 in MT-2 cells even when these cells were not stimulated with IL-2, whereas in YT cells, stimulation with IL-2 was required for substantial Jak3 association with $\gamma_c$. Similar results indicated that Jak3 and IL-2Rβ were constitutively associated in MT-2 cells but not in YT cells. Again, Jak3 and IL-2β coprecipitated from YT cell lysates following IL-2 stimulation. This indicated that at least some of the IL-2 receptor complexes appear to be constitutively assembled in cell lines transformed with HTLV-I.

As detailed in the following Example, we also discovered that the Jak3 and Stat5 proteins also coprecipitated from HTLV-I-transformed cells.

Example 6 describes the methods used to demonstrate constitutive association of Jak3 and Stat5.

EXAMPLE 6

Constitutive Associations of Stat5 and IL-2 Receptor Subunits in HTLV-I-transformed Cells Lysates of HTLV-I transformed HUT-102B2 cells that were left as untreated controls or stimulated with 2 nM IL-2 for 10 minutes were immunoprecipitated with antisera to Stat5 (anti-Stat5) or to Jak3 (anti-Jak3) and blotted with the 4G10 anti-phosphotyrosine antibody according to standard procedures.

Autoradiographic results indicated bands representing Jak3 and Stat5 in lanes corresponding to lyates from uninduced control and IL-2 stimulated HUT-102B2 cells. The Jak3 bands appeared between the 97 kDa and 200 kDa molecular weight markers, and were larger in molecular weight than the Stat5 band.

In a complementary procedure, proteins from lysates of MT-2 cells that were untreated controls or stimulated with 2 nM IL-2 for 10 minutes were immunoprecipitated with antiserum to Stat5 or antiserum to Jak3 and blotted with anti-Jak3 antiserum. Results indicated that the anti-Stat5 antiserum coprecipitated Jak3. This finding was consistent with a direct Jak-Stat interaction. In contrast to our ability to coprecipitate Jak3 and Stat5, we have not been able to coprecipitate Jak3 and Stat3. Although none of the HTLV-I-transformed T cell lines we have studied produced IL-2, some, such as HUT-102B2, can produce IL-15, a T cell growth factor that also activates Stat3 and Stat5 in PHA-treated PBL, and whose receptor contains IL-2Rβ and $\gamma_c$. The possible role of IL-15 in Stat protein activation in T cells transformed with HTLV-I was suggested by the ability of anti-IL-2Rβ mAb (R&D Systems No. 27302.1) that blocks IL-2 and IL-15 binding to diminish (by approximately 30%) but not abrogate the constitutive nuclear complexes detected in MT-2 cells.

Our results indicated that, in addition to constitutive association of Jak3 and IL-2Rβ in HTLV-I transformed cells, Jak3 and Stat5 were also constitutively associated.

In vitro, the transition from IL-2 dependence to IL-2 independence spans an average period of from between 6 and 12 months after HTLV-I infection of normal human cord blood or PBL. We therefore analyzed Jak kinases and Stat proteins in HTLV-I-infected cord blood lymphocytes both in the early IL-2-dependent phase (N1186 cells) and after a period of 11 months (N1186–94 cells) when their dependency on IL-2 had diminished, even though the cells were not producing IL-2.

Example 7 describes the methods used to demonstrate that HTLV-I infected cells progressed toward a condition of constitutive Stat protein activation that correlated with a state of growth factor independence.

EXAMPLE 7

Time-Dependent Acquisition of Constitutive Jak3 Tyrosine Phosphorylation, Jak3IL-2R Association, and Nuclear Stat Protein Binding Activity in HTLV-I Infected Cells N1186 cells were established by coculture of normal human cord blood lymphocytes with thawed peripheral blood mononuclear cells from a patient with adult T cell leukemia. Cells were maintained in medium containing IL-2 (20 U/ml). N1186–94 cells were derived from N1186 cells that had been maintained for 11 months in culture, during which time the IL-2 concentration was gradually lowered to 3 U/ml. Cells were grown in RPMI 1640 containing 10% FBS, washed, cultured for 4 hours in RPMI 1640 containing 1% FBS, and then resuspended in RPMI 1640 containing 10% FBS for 1 hour before stimulation with 0 or 2 nM IL-2. Nuclear extracts were prepared and EMSAs were performed using the FcγRI probe described above using standard procedures.

Autoradiographic results indicated that very little if any Stat binding activity was detectable in unstimulated N1186 cells, while N1186–94 cells contained constitutive binding activity. More specifically, none of the FcγRI probe was detectably shifted using extracts from untreated control N1186 cells. In contrast, lanes on the autoradiograph corresponding to extracts from IL-2 stimulated N1186 cells, as well as from control and IL-2 stimulated N1186–94 cells gave rise to strongly shifted bands. IL-2 stimulation of both cell populations led to increased Stat binding activity.

These results indicated that HTLV-I infected cells progress from a condition in which the Stat factors are not activated to a condition in which the Stat factors are constitutively activated in the later phase after HTLV-I transformation. Nevertheless, even cells in the later stages of HTLV-I transformation retained the ability to respond to IL-2 stimulation.

In parallel with the acquisition of constitutive Stat protein activation in N1186–94 cells, these cells exhibited a low level of constitutive tyrosine phosphorylation of Jak3. This level of phosphorylation was, however, less than that observed for long-term HTLV-I-transformed cell lines, such as MT-2 cells. To conduct this experiment, N1186, N1186–94 and PHA-treated PBL were left as untreated controls or stimulated with 2 nM IL-2 for 10 minutes. Proteins from call lysates were immunoprecipitated with antiserum to Jak3 and blotted with the 4G10 anti-phosphotyrosine antibody according to standard procedures. Autoradiographic results indicated no detectable Jak3 band in extracts from untreated control PBL or N1186 cells, but a weak Jak3 signal in extracts from N1186–94 cells. Strong Jak3 signals were detected in extracts from all three cell types following IL-2 stimulation. Interestingly, we found that Jak3 tyrosine phosphorylation was more strongly induced by IL-2 in N1186–94 cells than in MT-2 cells.

To determine the status of the interaction between Jak3 and $\gamma_c$ in cells approaching the later stages of HTLV-I transformation, samples of N1186 and N1186–94 cells were left as untreated controls or stimulated with 2 nM IL-2 for 10 minutes. Proteins were immunoprecipitated with antiserum R878 to $\gamma_c$ and blotted with antiserum to Jak3. Autoradiographic results indicated no detectable Jak3 band in immunoprecipitates from N1186 cells. However, bands representing Jak3 were easily observed in immunoprecipitates from untreated control N1186–94 cells, and in IL-2 stimulated N1186 and N1186–94 cells. Thus, as in MT-2 cells, N1186–94 cells exhibited constitutive association of $\gamma_c$ with Jak3 and of IL-2Rβ with both Jak3 and $\gamma_c$.

Since our original experiments were conducted, N186–94 cells have progressed to be completely IL-2 independent. Correspondingly, the level of constitutive Stat binding activity has increased. This evidence strongly supports the foregoing conclusion that HTLV-I infected T cells progress, with time, to constitutively activate the Jak-Stat signalling pathway.

Although the mechanisms by which HTLV-I transformation induces activation of the Jak-Stat pathway are not completely understood, our correlation of the constitutive Jak-Stat pathway with the acquisition of IL-2 independence in HTLV-I-transformed cells provides an additional insight into the mechanisms underlying the molecular basis of HTLV-I-mediated leukemogenesis. Activation of Jaks and Stats may be a strategy used by a number of viruses to mediate cell growth.

We reasoned that drugs which inhibited constitutive activation of the Jak-Stat signalling pathway in HTLV-I transformed cells would have clear therapeutic utility. We further reasoned that a molecular level understanding of events involved in activating the Jak-Stat pathway would contribute to methods of drug discovery. As a result, we endeavored to dissect the Jak-Stat pathway by transfecting site directed mutants of the genes encoding the IL-2 receptor components.

To determine if tyrosine residues in the IL2Rβ cytoplasmic domain were required for IL-2 induced cellular proliferation, expression constructs directing the production of wild-type or mutated forms of IL-2Rβ were transfected into IL-3 dependent 32D cells. The 32D cell line lacks endogenous IL-2Rβ but can proliferate in response to IL-2 after IL-2Rβ is transfected and expressed in these cells (Otani et al., Proc. Natl. Acad. Sci. USA 89:2789 (1992)).

As used herein, the following nomenclature is employed to refer to the various expression constructs encoding IL-2Rβ proteins having wild-type sequences, or bearing one or more tyrosine point mutations. βYYYYYY and βFFFFFF, respectively, indicate IL-2Rβ constructs having tyrosines (Y) or phenylalanines at positions Y338, Y355, Y358, Y361, Y392 and Y510. Similar nomenclature is used for reference to other IL-2Rβ constructs. Thus, βYFFFYY encodes an IL-2Rβ protein having phenylalanine residues at amino acid positions 355, 358 and 361. βFYYYFF encodes an IL-2Rβ protein having phenylalanine residues at amino acid positions 338, 392 and 510. βFFFFYY encodes an IL-2Rβ protein having phenylalanine residues at amino acid positions 338, 355, 358 and 361. βYYYYFF encodes an IL-2Rβ protein having phenylalanine residues at amino acid positions 392 and 510.

Example 8 describes the methods used to identify critical tyrosine residues on IL-2Rβ that are required for IL-2 stimulated cellular proliferation.

EXAMPLE 8

Tyrosines Y338, Y392 and Y510 of IL-2Rβ Required for Maximal IL-2 Induced Proliferation The IL-2Rβ coding region was mutated using the ALTERED SITES in vitro Mutagenesis System (Promega). Oligonucleotides used in this procedure were designed to change tyrosine (TAC) to phenylalanine (TTC, underlined) codons at Y338, 5'-ACCAACCAGGGTTTCTTCTTCTTCCAC-3' (SEQ ID NO:6); Y355Y358, and Y361, 5'-ATAGAGGCCTGCCAGGTGTTCTTTACTTTCGA CCCCTTCTCAGAGGAAGACCCTGATG-3'(SEQ ID NO:7); Y392, 5'-GAGGACGACGCCTTCTGCACCTTCCCCTCCAGG-3'(SEQ ID NO:8); or Y510, 5'-AACACTGATGCCTTCTTGTCCCTCCAA-3' (SEQ ID NO:9). Oligonucleotides were also combined to create multiple mutations. Mutants were confirmed by DNA sequencing (SEQUENASE, USB), subcloned into pME18S, linearized, and electroporated with pCDNA3neo (In Vitrogen) into 32D cells using a GENE PULSER (Bio-Rad) at 300 V and 960 μF. Cells were maintained in RPMI 1640 medium supplemented with 10% fetal bovine serum (FBS), $10^{-5}$ M β-mercaptoethanol (β-ME), and 5% WEHI-CM. Stable transfectants were selected in 1 mg/ml G418 (Gibco BRL) using standard laboratory techniques. IL-2Rβ expression was assessed by flow cytometry using FITC-conjugated anti-IL-2Rβ mAb (Endogen).

Figure 1:
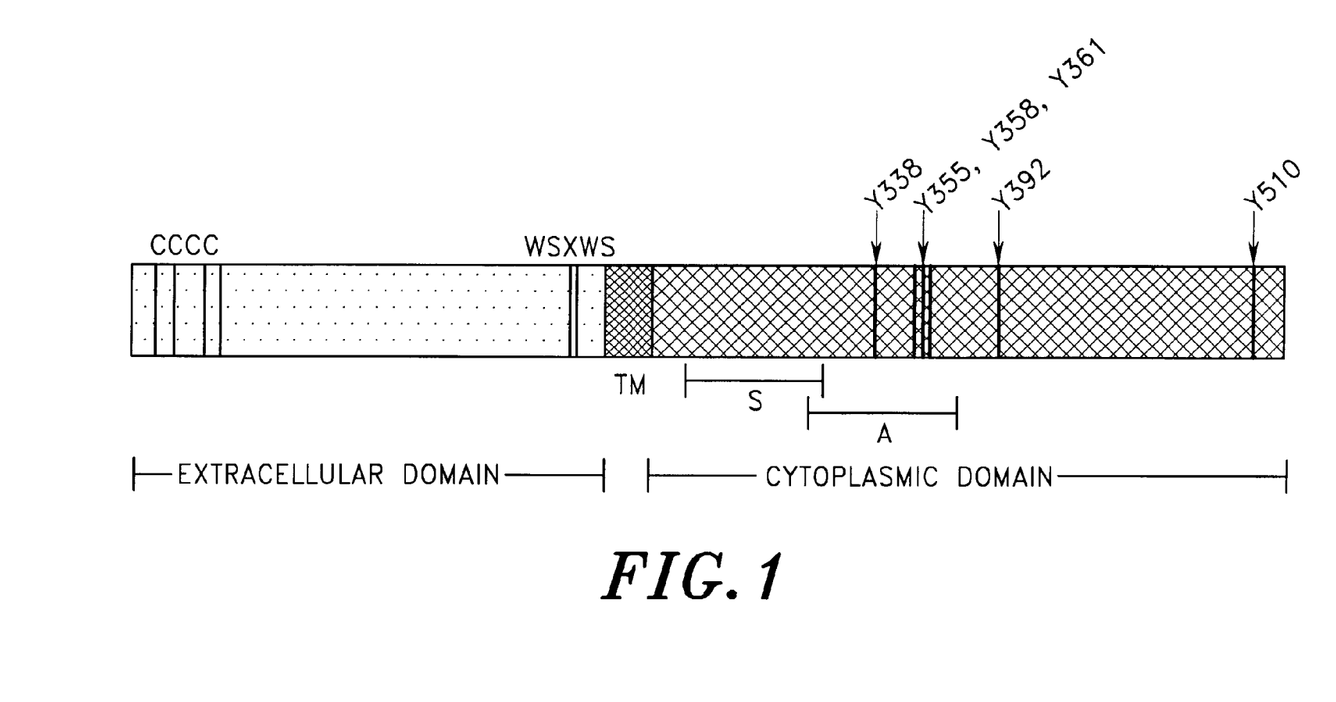
FIG. 1 is a schematic diagram of the IL-2Rβ protein. The relative positions of six tyrosine residues (Y338, Y355, Y358, Y361, Y392 and Y510) are indicated.

The IL-2Rβ protein is schematically depicted in FIG. 1. The diagram illustrates the locations of four conserved cysteines and the WSXWS motif in the extracellular domain that are characteristic of cytokine receptor superfamily members. Also illustrated are the transmembrane (TM) domain, the regions deleted in the IL-2Rβ S and A mutants, and the positions of tyrosines in the cytoplasmic domain.

Figure 2A:
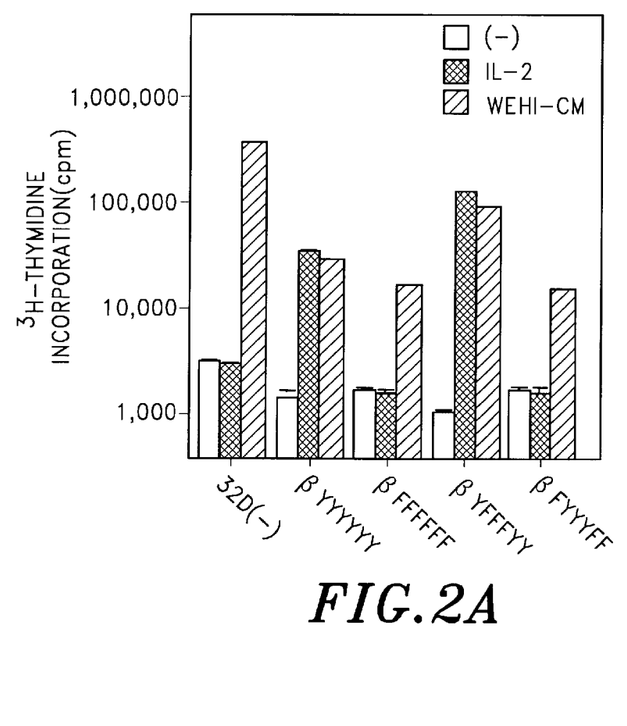
FIGS. 2A and 2B are a set of bar graphs representing the results from cellular proliferation assays.
Figure 2B:
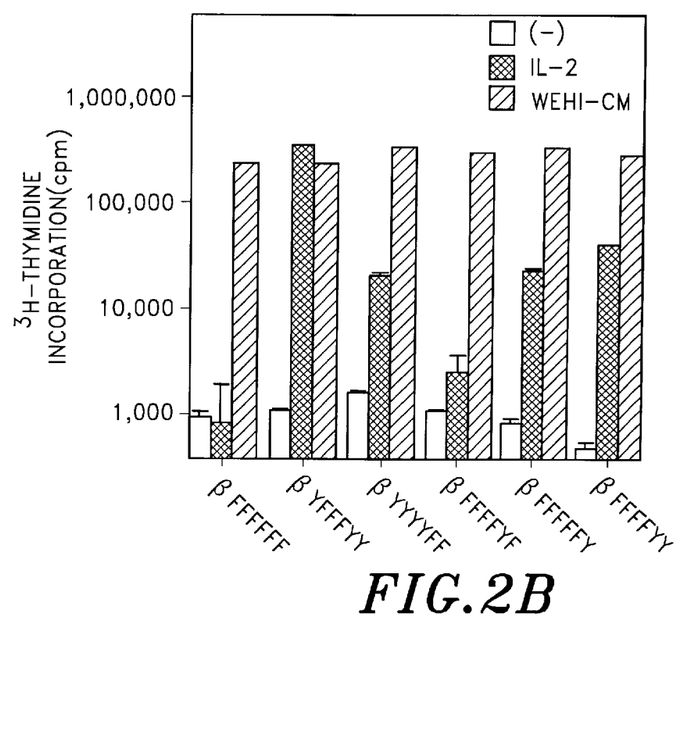

Transfection results presented in FIG. 2a and 2b indicated that three of the six IL-2Rβ tyrosine residues were required for a maximal IL-2 induced cellular proliferative response. As indicated in the Figure, 32D cells not transfected (32D (−)) or transfected with the indicated constructs were treated with medium alone (open bars), 10 nM IL-2 (solid bars), or 5% WEHI-3B conditioned medium (WEHI-CM) as a source of IL-3 (an amount sufficient to induce maximal proliferation). Thymidine incorporation was determined as described by Nakamura et al., in Nature 369:330 (1994), except that cells were pulsed with 1 μCi $^3$H-thymidine. For each transfectant, at least three high expressing clones were assayed.

Simultaneous mutation of all six tyrosines in the IL-28β cytoplasmic domain to phenylalanines abolished the proliferative response to IL-2 (compare βYYYYYY and βFFFFFF, FIG. 2a, 2b). Mutation of the three clustered tyrosines (Y355, Y358 and Y361) did not decrease thymidine incorporation (βYFFFYY, FIG. 2a, 2b). In contrast, mutation of the three tyrosine residues at positions Y338, Y392 and Y510 abolished IL-2 responsiveness, as indicated in FIG. 2a. This result indicated that one or more of Y338, Y392 and Y510 contributed to IL-2 induced proliferation.

We also found that mutation of Y392 or Y510 (βYYYYFY and βYYYYYF) had little effect on the ability of IL-2 stimulation to induce cellular proliferation. However, when both Y392 and Y510 were mutated (βYYYYFF), IL-2 induced proliferation was less than 10% of IL-3 induced proliferation as indicated by the results presented in FIG. 2b. Y510 appeared to have a stronger effect on proliferation than did Y392, since cells expressing a construct that retained only Y510 (βFFFFFY) proliferated better than cells expressing a construct that retained only Y392 (βFFFFYF), also as indicated in FIG. 2b. The fact that cells expressing βYYYYFF proliferated to some extent suggested that at least one of the first four tyrosines also could mediate proliferation. Indeed, the most membrane proximal tyrosine, Y338, was important since, as presented in FIG. 2a, βFYYYFF did not mediate proliferation. The results presented in FIG. 2b indicated that both βFFFFYY and βYYYYFF mediated suboptimal proliferation whereas βYFFFYY mediated full proliferation. This finding was consistent with a model wherein Y338, Y392 and Y510 together coordinate two or more cooperating signalling pathways.

Having established the importance of tyrosine residues Y338, Y391 and Y510, we proceeded to examine whether these tyrosines were also phosphorylation targets.

Example 9 describes the methods used to demonstrate that Y338, Y392 and Y510 of IL-2Rβ were phosphorylation substrates.

EXAMPLE 9

Phosphorylation of Y338, Y392 and Y510 of IL-2Rβ

Fifty million 32D cells transfected with βYYYYYY, βFFFFFF, or βYFFFYY were incubated in the absence or presence of 2 nM IL-2 for 15 minutes at 37° C. Cell were then lysed, immunoprecipitated with humanized Mikβ1 mAb to IL-2Rβ(hMik1, provided by J. Hakimi, Hoffmann LaRoche.) Immunoprecipitates were immunoblotted with the 4G10 anti-phosphotyrosine mAb (UBI) and detected by enhanced chemiluminescence (Amersham).

Results indicated a nearly undetectable basal level of tyrosine phosphorylation of IL-2Rβ when 32D cells were transfected with wild-type IL-2Rβ (βYYYYYY) or with a construct containing Y338, Y392 and Y510 (βYFFFYY). However, phosphorylation of the βYFFFYY IL-2Rβ substrate increased following stimulation with IL-2. This was evidenced by the presence of a band that migrated between the 69 kDa and 97 kDa markers on the autoradiograph in the lane corresponding to IL-2 stimulated βYFFFYY transfectants. As expected, no signal was detected with lysates from cells expressing a construct in which all tyrosines were mutated (βFFFFFF). Thus, an IL-2Rβ protein having tyrosines Y338, Y392 and Y510 was inducibly phosphorylated following IL-2 stimulation. Conversely, an IL-2Rβ protein that lacked six of the tyrosine residues was not phosphorylated.

In order to further investigate the identity of the tyrosine residues that were phosphorylated in response to IL-2 stimulation, 32D cells separately transfected with the βFYYYFF, βFFFFFF, βYYYYFF, βFFFFYY, βYFFFYY and βYYYYYY constructs were treated with 10 nM IL-2 for 15 minutes, lysed, immunoprecipitated with TU11 anti-IL-2Rβ mAb, and immunoblotted with the 4G10 anti-phosphotyrosine mAb according to standard procedures.

Results indicated that IL-2Rβ was tyrosine phosphorylated in cells that expressed the βYYYYFF, βFFFFYY, βYFFFYY or βYYYYYY constructs. More specifically, immunoprecipitates from these transfectants gave rise to single bands that migrated between the 69 kDa and 97 kDa markers on the autoradiograph. Thus, of the constructs tested, only those that retained one or more of tyrosines Y338, Y392 and Y510 were inducibly phosphorylated by IL2 stimulation. A transfectant containing only Y355, Y358 and Y361 (βFFYYYFF) was not phosphorylated.

Since Jak1 is known to physically associate with IL-2Rβ, we investigated whether Y338, Y392 and Y510 were substrates for the Jak1 protein tyrosine kinase. As illustrated in the following Example, COS-7 cells were transfected with Jak1 and IL-2Rβ expression constructs, lysed, and IL-2Rβ was immunoprecipitated under conditions, described by Russell at al., in Science 266:1042 (1994), which allowed for coprecipitation with Jak1. After in vitro kinase assays were performed using unlabeled ATP, IL-2Rβ phosphorylation was assessed by immunoblotting with the 4G10 anti-phosphotyrosine mAb.

Example 10 describes the methods used to demonstrate that tyrosine residues Y338, Y392 and Y510 of IL-2Rβ were phosphorylated by Jak1.

EXAMPLE 10

Jak1 Dependent Phosphorylation of Y338, Y392 and Y510 of IL-2Rβ

COS-7 cells were cotransfected using DEAE dextran with either the wild-type or mutant IL-2Rβ constructs and with an expression plasmid without insert or with an insert encoding Jak1. After 48–72 hours, cells were lysed as previously described, and clarified extracts were immunoprecipitated using hMikβ1. In vitro kinase assays were performed by standard methods using unlabeled ATP, followed by immunoblotting with the 4G10 mAb.

Results of the immunoprecipitation and immunoblotting procedure indicated that mutation of all six tyrosines (βFFFFFF) or just Y338, Y392 and Y510 (βFYYYFF) eliminated IL-2Rβ phosphorylation. However, a construct that additionally retained Y338 (βYYYYFF) was phosphorylated by Jak1. Although mutants retaining only Y392 (βFFFFYF) or Y510 (βFFFFFY) were poorly phosphorylated, a construct retaining both Y392 and Y510 was more heavily phosphorylated. This result indicated a possible synergistic effect in the phosphorylation of Y392 and Y510 by Jak1. Jak3 is known to associate with IL-2Rβ more weakly than does Jak1 (Russell et al., Science 266:1042 (1994)), and correspondingly, we found that it was less potent than Jak1 in its ability to phosphorylate IL-2Rβ. Thus, our results proved that Y338, Y392 and Y510 can all be phosphorylated by Jak1.

Those having ordinary skill in the art will appreciate that IL-2 has been shown to activate both the Ras and Jak-Stat signalling pathways. The results disclosed in the following Example unexpectedly indicated that Y338, Y392 and Y510 differentially couple to these two signalling pathways.

Example 11 describes the methods used to demonstrate the coupling of the Ras and Jak-Stat signalling pathways through IL-2Rβ.

EXAMPLE 11

Coupling of Y338 to Shc and Y392 and Y510 to the Jak-Stat Pathway 32D cells transfected with expression plasmid constructs that encoded the βYYYYYY, βFFFFFF, βFYYYFF, βYYYYFF, βFFFFYY mutant proteins. Lysates prepared from the transfectants were immunoprecipitated with hMikβ1 or TU11 anti-IL-2Rβ and then immunoblotted with anti-Shc. Shc is an adaptor protein that can initiate activation of the Ras pathway (Pastor et al., Immunol. Today 16:159 (1995)), associates with IL-2Rβ (Ravichandran et al., J. Biol. Chem. 269:1599 (1994)) and is tyrosine phosphorylated in response to IL-2 (Burns et al., J. Biol. Chem. 268:17659 (1993)). Cells expressing wild-type IL-2Rβ were analyzed both before and after stimulation with either 2 nM IL-2 or 10 nM IL-2 for 15 minutes.

Results indicated that only those constructs which retained Y338 showed significant Shc association. More specifically, in addition to the βYYYYYY transfectants (with or without IL-2 stimulation), only βYYYYYY and βYYYYFF transfectants that had been stimulated with 10 nM IL-2 exhibited Shc protein bands between 46 kDa and 69 kDa on the autoradiograph. Although Shc was constitutively associated with IL-2Rβ in 32D cells, perhaps because of the basal phosphorylation of IL-2Rβ, phosphorylation of Shc was only detected after IL-2 stimulation. To make this determination, parental 32D cells or cells expressing wild-type IL-2Rβ were left as untreated controls or stimulated with 2 nM IL-2 for 15 minutes. Lysates from these cells were immunoprecipitated with 4G10 and immunoblotted with anti-Shc (UBI). The requirement of Y338 for IL-2-induced phosphorylation of Shc may explain why Y338 was important for proliferation.

Example 12 describes the methods used to demonstrate which of the IL-2Rβ tyrosine residues played a role in the inducible activation of the Stat proteins.

EXAMPLE 12

Tyrosines Y392 and Y510 are Required for IL-2 Induced Activation of Stat Proteins Wild-type 32D cells or cells transfected with βYYYYYY, βFFFFYF, βFFFFFY, βFFFFYY, βYYYYFF or βFFFFFF IL-2Rβ constructs were washed, starved of growth factor for 4 hours in RPMI 1640 made 1% FBS and $10_{-5}$ M β-ME, and then left untreated or stimulated with 2 nM IL-2 for 30 minutes at 37° C. Total cell extracts were analyzed by EMSAs using a $^{32}$P-labeled FcγRI-GAS probe.

Results indicated that constructs containing either Y392 or Y510 or both could mediate IL-2 induced Stat DNA binding activity. Conversely, constructs in which all six tyrosines or just Y392 and Y510 were mutated had markedly diminished binding activity in the immunoprecipitation and immunoblotting assay. Thus, Y392 and Y510 were important for Stat protein activation. The correlation between the large decreases in proliferation and Stat protein activation resulting from mutation of Y392 and Y510 (βYYYYFF) suggested that the Jak-Stat pathway was essential for maximal IL-2 induced proliferation.

The results disclosed herein indicated that Y338, Y293, and Y510 each contributed to a proliferative signal and together mediated a full proliferative response to IL-2 stimulation. Y392 and Y510 mediated Stat protein activation, while Y338 mediated tyrosine phosphorylation of Shc. These facts establish a basis by which IL-2Rβ couples to both the Jak-Stat and Ras pathways. The roles of the various IL-2Rβ tyrosine residues is summarized in Table 1.

TABLE 1

Summary of the functional responses of 32D cells expressing wild type or mutated forms of IL-2Rβ in response to IL-2

| IL-2Rβ mutant | Proliferation | IL-2Rβ phos-phorylation | Stat activation | Shc phos-phorylation |
| --- | --- | --- | --- | --- |
| βYYYYYY | +++ | + | + | + |
| βFFFFFF | − | − | − | − |
| βYFFFYY | +++ | + | + | + |
| βFYYYFF | − | − | − | − |
| βFFFFYY | + | + | + | − |
| βYYYYFF | + | + | − | + |

Figure 3:
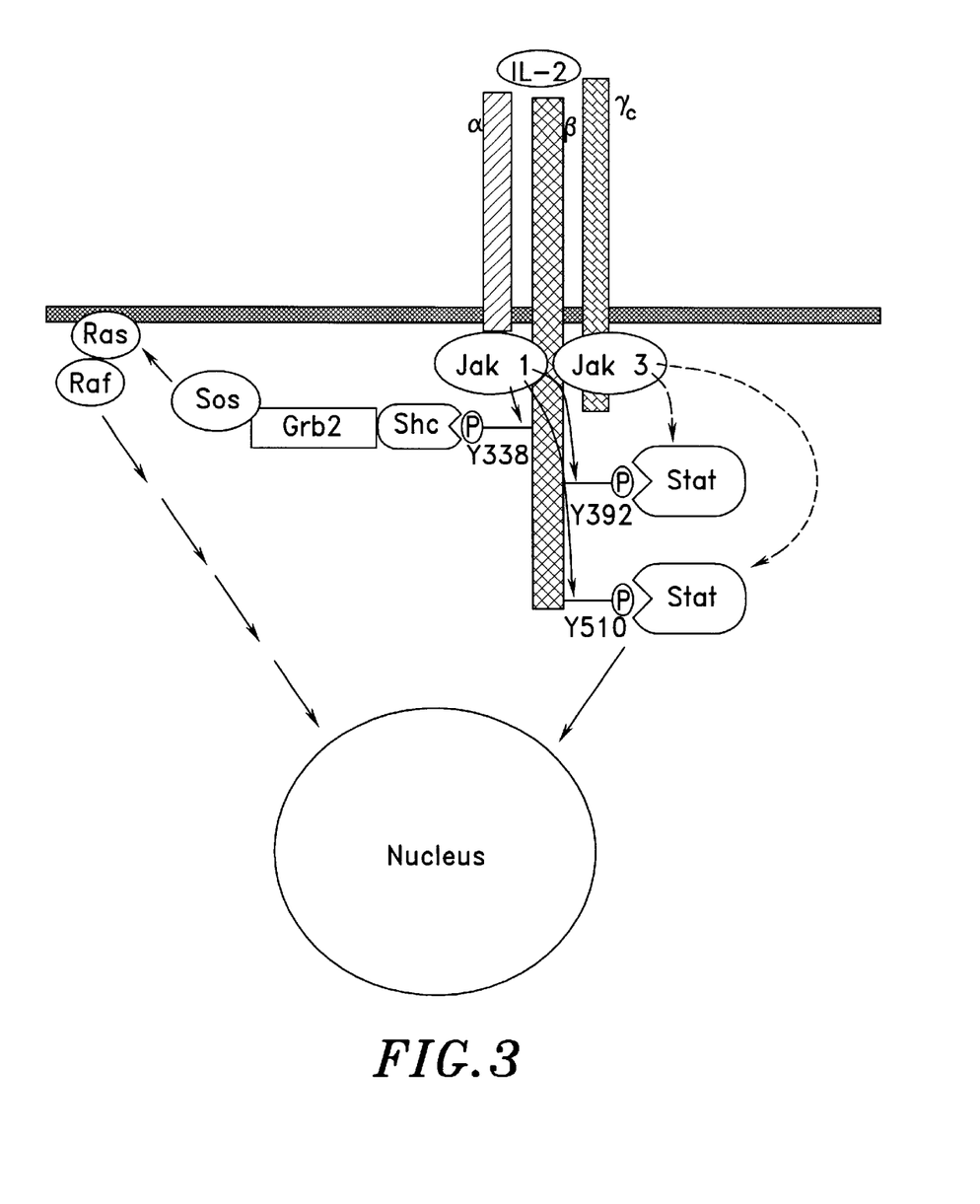
FIG. 3 is a schematic diagram showing the functional relationship between components of the IL-2 receptor.

FIG. 3 schematically depicts the IL-2Rβ mediated coupling between the Shc- and Jak-Stat pathways. As illustrated, Jak1 associates with IL-2Rβ and can phosphorylate Y338, Y392 and Y510 (bold solid arrows). Shc binds to Y338 and couples to Grb2 and Sos, thereby activating Ras. Stat proteins dock at Y392 and Y510. Jak3 primarily associates with $γ_c$ but also interacts with IL-2Rβ. It is unclear which kinase phosphorylates the Stat proteins. We hypothesize that Jak3 plays a role (bold dashed arrows). Not shown are Y355, Y358, and Y361 since their roles, if any, in contributing to IL-2 induced proliferation remain unclear. Although Lck and Syk have been reported to associate with IL-2Rβ (Taniguchi et al., *Science* 268:251 (1995)); they are omitted from this schematic to focus on the pathways which we demonstrated to be involved in IL-2 induced proliferation.

We also demonstrated that synthetic peptides which encompassed the domains of IL-2Rβ that included either Y392 or Y510 could inhibit the DNA binding activity of activated Stat transcription factors in vitro. The experimental procedure employed to make this demonstration was based on the ability of activated stat protein dimers to bind a DNA probe which harbored a GAS motif. We believe that Stat dimers are in an equilibrium of formation and dissociation, and that dissociated monomers cannot reassociate to form active dimers in the presence of the inhibitory peptides. Since dimerization of Stat3 and/or Stat5 into homodimers and/or heterodimers is required for DNA binding activity, dissociated monomers cannot participate in gene activation. As disclosed below, the synthetic peptides that inhibited Stat protein dimerization and DNA binding activity embody features that would be expected of agents that inhibit the Jak-Stat signalling pathway. Our peptide competition procedures and results have been published in *Immunity* 2:331 (1995), the disclosure of which is hereby incorporated by reference.

Example 13 describes the methods used to demonstrate the inhibition of Stat DNA binding in EMSAs using synthetic peptides.

EXAMPLE 13

Peptide Competition for Stat Binding

Phosphorylated peptides for competition experiments were synthesized with an Applied Biosystems 431A peptide synthesizer using FMOC chemistry and HBTU activation. FMOC phosphotyrosine was from Nova Biochemical. Peptide βY392 had the amino acid sequence, EDDAYCTF-PSBD (SEQ ID NO:10), where the tyrosine residue was phosphotyrosine. Peptide βY510 had the amino acid sequence, NTDAYLSLQELQ (SEQ ID NO:11), where the tyrosine residue was phosphotyrosine. Peptides were purified by reverse phase C18 high pressure liquid chromatography and quantitated using a PICOTAG system (Waters). For peptide inhibition experiments, peptides (100 μM) were preincubated with nuclear extracts for 30 minutes at room temperature prior to the addition of probe. DNA probes used in the EMSA protocol are described in Example 1.

Results indicated that, when the βY510 synthetic peptide competitor was added to the nuclear extract before probe addition and binding, as little as 20 μM tyrosine-phosphorylated peptide inhibited binding. When βY392 was used, 100 μM of competitor was required to produce complete inhibition. More specifically, nuclear extracts prepared from IL-2 induced PBL that had not been treated with PHA gave rise to an intense band on the EMSA autoradiograph in the absence of added peptide. When a βY338 synthetic peptide having the amino acid sequence TNQGY$^P$FFF-HLPD (SEQ ID NO:12) was used as a competitor, the intensity of the band did not change. This negative result demonstrated that simple addition of a synthetic peptide failed to inhibit DNA binding. Thus, any inhibition observed in the assay must have been specific inhibition and not nonspecific inhibition of DNA binding. When either of peptides βY392 or βY510 was added to the extract, the intensity of the shifted band decreased dramatically. This decrease in the intensity of the shifted species represented the expected result to be obtained for an agent that inhibited the binding of activated Stat dimers to cognate DNA binding motifs. These results also confirmed that peptide fragments representing segments of the IL-2Rβ chain, in the region demonstrated hereinabove to be required for Stat activation, could specifically interact with Stat proteins and disrupt activated dimers, preventing binding to DNA.

Similar results were obtained using extracts from preactivated PBL, except that only the upper complex of a doublet band which appeared on the autoradiograph was eliminated when extracts were preincubated with either βY392 or FY510. The peptide competitions were specific, since non-phosphorylated βY510 did not inhibit formation of the nuclear complexes induced by IL-2 in fresh or preactivated PBL. Importantly, a tyrosine-phosphorylated peptide spanning IL-7RY409 and having the amino acid sequence, QEEAY$^P$VTMSSFY (SEQ ID NO:13) also inhibited Stat protein binding. This indicated that the domain of the IL-7R chain that included position Y409 represented a contact site for stat proteins.

Example 14 describes a method of identifying drugs that inhibit the binding of Stat dimers to DNA target motifs.

EXAMPLE 14

Method of Identifying Stat3/Stat5 Inhibitors

A nuclear extract of HTLV-I transformed MT-2 cells is first obtained by standard methods. A sample of the extract is incubated with a DNA probe containing a GAS motif. One example of such a DNA probe is an FcγRI probe having the nucleotide sequence of SEQ ID NO:1. The incubation mixture is then electrophoretically separated and the resulting gel exposed to X-ray film. The resulting autoradiograph has one or more bands representing slowly migrating DNA-protein complexes. This control lane indicates the mobility of the complex between the DNA probe and the activated Stat proteins. The complexes contain Stat3 homodimers, Stat5 homodimers and/or heterodimers.

The above procedure is repeated except that test compounds are also added. Each test compound is added to an aliquar of nuclear extract before the addition of the labeled DNA probe. The mixtures are separated, run on a separate lane of a gel, and autoradiographed. If a test compound does not result in a change in the bands seen in the control lane then the test compound is not a candidate drug. On the other hand, if a change in intensity in at least one of the bands is seen, then the compound is a candidate drug. The lane on the autoradiograph representing the sample incubated with the first test compound has bands of similar mobility and intensity as the bands observed in the control lane. This result indicates that the first test compound does not inhibit the binding of a Stat protein dimer to the DNA probe. In contrast, the lane on the autoradiograph representing the sample incubated with the second test compound has at least one band of diminished intensity relative to the bands observed in the control lane. This decreased band intensity indicates that the second test compound inhibits the binding of stat protein to the DNA probe. Thus, the second test compound is a candidate drug for inhibiting the activity of the Jak-Stat signalling pathway.

Those having ordinary skill in the art will appreciate that alternative assays can be employed to identify agents that inhibit the Jak-Stat signalling pathway. Such assays can, for example, be used to identify agents that inhibit the interaction between the IL-2Rβ chain, or peptide fragments thereof, and Stat protein. If the binding assay is carried out using either IL-2Rβ or peptide fragments of IL-2Rβ that include Y392 or Y510, the tyrosine residues corresponding to positions 392 and 510 must be phosphotyrosines.

Example 15 describes another method of identifying agents that inhibit the Jak-Stat signalling pathway by interfering with the interaction between the Stat proteins and synthetic peptides that harbor docking sites on the IL-2Rβ chain.

EXAMPLE 15

Method of Identifying Inhibitors of the Jak-Stat Signalling Pathway

Purified Stat5 protein is immobilized to the wells of a plastic 96 well microtiter plate by standard methods. Non-specific protein binding sites on the plastic are blocked by methods that will be appreciated by those having ordinary skill in the art. A synthetic peptide having the amino acid sequence of SEQ ID NO:10 is next obtained. The tyrosine residue in the peptide is a phosphotyrosine residue and is radiolabeled. Three peptide binding mixtures are prepared. The control mixture contains the labeled peptide in an aqueous binding buffer. The second binding mixture is identical to the control, but additionally contains a first test compound to be screened as an inhibitor of Jak-Stat interaction. The third binding mixture is identical to the control, but additionally contains a second test compound to be screened as an inhibitor of Jak-Stat interaction. The peptide binding mixtures are added to the wells having Stat5 protein immobilized thereon. Nonspecifically bound peptide is removed from all three wells. immobilized radiolabeled peptide is quantitated by standard means. Reduction in the level of label is indicative of inhibition of the Jak-Stat pathway.

Results indicate the control well has retained a substantial quantity of the radiolabeled peptide. The second well has similarly retained a substantial quantity of the radiolabeled peptide. This indicates the first test compound had substantially no effect on the Stat5-peptide interaction, and is not a candidate drug for inhibiting the Jak-Stat signalling pathway. The third well has retained substantially none of the radiolabeled peptide. This indicates the second test compound efficiently blocked the Stat5-peptide interaction, and is a candidate drug for inhibiting the Jak-Stat signalling pathway.

Drugs that inhibit the Jak-Stat signaling pathway are candidates for the treatment of cellular proliferative disorders caused by constitutive activation of this signalling pathway. Such drugs are believed, for example, to be useful in the treatment of adult T cell leukemia brought on by infection with HTLV-I. Herein we have disclosed that the Jak-Stat pathway is constitutively activated in HTLV-I infected T cells that have progressed to a stage of growth factor independence. We have also demonstrated that the same tyrosine residues which are critical for maximal IL-2 induced proliferation are also required for activation of the Stat3 and Stat5 transcription factors. Thus, it is believed that inhibition of this pathway can lead to a generalized treatment of proliferative disorders, including several types of cancer.

Example 16 describes how a drug identified as an inhibitor of the Jak-Stat signalling pathway can be used to treat an HTLV-I infected individual afflicted with adult T cell leukemia.

EXAMPLE 16

Therapeutic Administration of Drugs that Inhibit the Jak-Stat Signalling Pathway An HTLV-I infected patient is first identified. A blood sample taken from the patient is found to contain an unusually high proportion of T cells. The patient is administered with a therapeutically effective dose of a composition comprising a drug that inhibits the Jak-Stat signalling pathway and a pharmaceutically acceptable carrier in a daily regimen. The carrier can, for example be a saline solution for intravenous administration, or a starch-based material for oral administration. The patient's T cell count is monitored over a period of several months and is found to approach normal range. The patient's lifetime is extended as a result of the drug administration.

Thus, Example 16 indicates that candidate drugs which inhibit the Jak-Stat pathway can effectively treat elevated T cells resulting from HTLV-I infection. HTLV-I infection also results in other manifestations, including skin infiltration.

Candidate drugs are also believed to be effective in treating these other manifestations of HTLV-I infection.

The foregoing demonstrates that identification of agents which inhibit the Jak-State pathway is useful for identifying candidate drugs for treatment of any of a variety of proliferative disorders, including leukemias caused by HTLV-I. Once candidate drugs are identified, pharmaceutical compositions for treatment of these disorders can be developed using techniques well known in the art. These techniques include the further testing of identified cadidate drugs for their ability to inhibit proliferation of affected cells and conventional dose-response studies.

Transplantation rejection is known to be mediated through IL-2 receptors. In fact, anti-IL-2R antibodies and IL-2/diptheria toxin conjugates have been used to treat. Interruption of any part of the IL-2 pathway would be useful in inhibiting transplant rejection. Thus, we believe that drugs identified through the methods of the present invention in which agents which block the Jak-stat pathway are identified are beneficial in the prevention of transplant rejection. In this regard, co-pending U.S. patent application Ser. No. 08/373,934 discloses the identification of immune modulators. This co-pending application is hereby incorporated by reference.

What is claimed is:

1. A method of identifying an agent as a candidate Jak-Stat pathway inhibitor by the steps of:
   (a) obtaining a control lysate prepared from HTLV-1 transformed cells, said control lysate containing IL-2 receptor components including Stat3, Stat5, IL-2Rβ and γc;
   (b) obtaining a test lysate prepared from HTLV-I transformed cells propagated in the presence of said agent, said test lysate containing IL-2 receptor components including Stat3 or Stat5, IL-2Rβ and γc;
   (c) quantitating in each of said lysates an interaction between IL-2Rβ and Stat3 or Stat5 ; and
   (d) identifying the agent as an inhibitor of the Jak-Stat pathway if the interaction quantitated in the quantitating step is greater in the control lysate than in the test lysate.

2. A method of identifying an agent as a candidate Jak-Stat pathway inhibitor, comprising the steps of:
   (a) obtaining an HTLV-1 transformed cell line identified as displaying activated Jak3; and
   (b) assessing the efficacy of said agent in inhibiting Jak3 activation, wherein a candidate Jak-Stat pathway inhibitor is identified if inhibition occurs.

3. The method of claim 2, wherein said assessing step is selected from the group consisting of inhibition of Jak3 tyrosine phosphorylation and inhibition of Jak3-IL-2Rγ interaction.

4. A method of identifying an agent as a candidate Jak-Stat pathway inhibitor, comprising the steps of:
   (a) obtaining an HTLV-1 transformed cell line identified as displaying activated Stat5; and
   (b) assessing the efficacy of said agent in inhibiting Stat5 activations, wherein a candidate Jak-Stat pathway inhibitor is identified if inhibition occurs.

5. The method of claim 4, wherein said assessing step is selected from the group consisting of inhibition of Stat5 tyrosine phosphorylation, inhibition of Stat5-IL-2Rβ interaction and inhibition of Stat5 interaction with a polynucleotide containing a Stat5 binding site.

6. A method of identifying an agent as a candidate Jak-Stat pathway inhibitor, comprising the steps of:
   (a) obtaining an HTLV-1 transformed cell line identified as displaying activated Stat3; and
   (b) assessing the efficacy of said agent in inhibiting Stat3 activation, wherein a candidate Jak-Stat pathway inhibitor is identified if inhibition occurs.

7. The method of claim 6, wherein said assessing step is selected from the group consisting of inhibition of Stat3 tyrosine phosphorylation, inhibition of Stat3-IL-2Rβ interaction and inhibition of Stat3 interaction with a polynucleotide containing a Stat3 binding site.

8. A method of identifying an agent as a candidate Jak-Stat pathway inhibitor, comprising the steps of:
   (a) providing a candidate Jak3 inhibitor; and
   (b) measuring the efficacy of the candidate inhibitor in inhibiting activation of Jak3 in an HTLV-1 transformed cell line, wherein a candidate Jak-Stat pathway inhibitor is identified if inhibition occurs.

9. The method of claim 8, wherein said measuring step is selected from the group consisting of inhibition of Jak3 tyrosine phosphorylation and inhibition of Jak3-IL-2Rγ interaction.

10. A method of identifying an agent as a candidate Jak-Stat pathway inhibitor, comprising the steps of:
    (a) providing a candidate Stat5 inhibitor; and
    (b) measuring the efficacy of the candidate inhibitor in inhibiting activation of Stat5 in an HTLV-1 transformed cell line, wherein a candidate Jak-Stat pathway inhibitor is identified if inhibition occurs.

11. The method of claim 10, wherein said measuring step is selected from the group consisting of inhibition of Stat5 tyrosine phosphorylation, inhibition of Stat5-IL-2Rβ interaction and inhibition of Stat5 interaction with a polynucleotide containing a Stat5 binding site.

12. A method of identifying an agent as a candidate Jak-Stat pathway inhibitor, comprising the steps
    (a) providing a candidate Stat3 inhibitor; and
    (b) measuring the efficacy of the candidate in inhibiting activation of Stat3 in an HTLV-1 transformed cell line, wherein a candidate Jak-Stat pathway inhibitor is identified if inhibition occurs.

13. The method of claim 12, wherein said measuring step is selected from the group consisting of inhibition of Stat3 tyrosine phosphorylation, inhibition of Stat3-IL-2Rβ interaction and inhibition of Stat3 interaction with a polynucleotide containing a Stat3 binding site.

14. A method of identifying an agent as a candidate Jak-Stat pathway inhibitor, comprising the steps of:
    (a) providing a candidate competitor of IL-2RβY392 tyrosine phosphorylated motif; and
    (b) measuring the efficacy of the candidate in inhibiting the binding of Stat5, wherein a candidate Jak-Stat pathway inhibitor is identified if inhibition occurs.

15. A method of identifying an agent as a candidate Jak-Stat pathway inhibitor, comprising the steps of:
    (a) providing a candidate competitor of IL-2RβY510 tyrosine phosphorylated motif; and
    (b) measuring the efficacy of the candidate in inhibiting the binding of Stat5, wherein a candidate Jak-Stat pathway inhibitor is identified if inhibition occurs.

16. A method of identifying an agent as a candidate Jak-Stat pathway inhibitor, comprising the steps of:
    (a) providing a candidate competitor of IL-7RY409 tyrosine phosphorylated motif; and
    (b) measuring the efficacy of the candidate in inhibiting the binding of Stat5, wherein a candidate Jak-Stat pathway inhibitor is identified if inhibition occurs.

17. A method of identifying an agent as a candidate Jak-Stat pathway inhibitor, comprising the steps of:
    (a) observing the activation of Stat5 by IL-2RβY392 tyrosine phosphorylated motif; and
    (b) assessing the efficacy of said agent in inhibiting Stat5 activation by IL-2RβY392, wherein a candidate Jak-Stat pathway inhibitor is identified if inhibition occurs.

18. A method of identifying an agent as a candidate Jak-Stat pathway inhibitor, comprising the steps of:
    (a) observing the activation of Stat5 by IL-2RβY510 tyrosine phosphorylated motif; and
    (b) assessing the efficacy of an agent in inhibiting Stat5 activation by IL-2RβY510, wherein a candidate Jak-Stat pathway inhibitor is identified if inhibition occurs.

19. A method of identifying an agent as a candidate Jak-Stat pathway inhibitor, comprising the steps of:
    (a) observing the activation of Stat5 by IL-7RY409 tyrosine phosphorylated motif; and
    (b) assessing the efficacy of an agent in inhibiting Stat5 activation by IL-7RY409, wherein a candidate Jak-Stat pathway inhibitor is identified if inhibition occurs.

20. A method of identifying an agent as a candidate Jak-Stat pathway inhibitor by the steps of:
    (a) obtaining a nuclear extract containing IL-2-activated Stat3 or IL-2-activated Stat5 transcription factors;
    (b) obtaining a labeled DNA probe containing at least one binding site for the activated transcription factors;
    (c) preparing control and test binding reactions, wherein each of said binding reactions contains a sample of the nuclear extract and a sample of the labeled DNA probe, and wherein the test binding reaction additionally contains said agent;
    (d) incubating the binding reactions to allow interaction between the DNA probe and the transcription factors;
    (e) quantitating the amount of interaction after incubating each of the binding reactions; and
    (f) identifying said agent as a Jak-Stat pathway inhibitor if the amount of interaction quantitated in the quantitating step is reduced in the test binding reaction when compared with the control binding reaction.

* * * * *